(12) United States Patent
Gray

(10) Patent No.: US 6,315,750 B1
(45) Date of Patent: Nov. 13, 2001

(54) ORTHOPEDIC LUMBAR TRACTION SITTING DEVICE

(76) Inventor: James T. Gray, 1724 Pine Ave., Los Osos, CA (US) 93402

( * ) Notice: Subject to any disclaimer, the term of this patent is extended or adjusted under 35 U.S.C. 154(b) by 0 days.

(21) Appl. No.: 09/641,641

(22) Filed: Aug. 21, 2000

Related U.S. Application Data

(60) Provisional application No. 60/158,150, filed on Oct. 8, 1999.

(51) Int. Cl.$^7$ ........................................... A61F 5/00
(52) U.S. Cl. ............................ 602/32; 602/36; 606/241
(58) Field of Search ..................... 602/32–36, 38, 602/19; 606/237, 240–242, 244; 297/353, 465; 128/845, 873–875; 482/95, 96, 131, 143, 907

(56) References Cited

U.S. PATENT DOCUMENTS

| | | | |
|---|---|---|---|
| 4,030,489 | * | 6/1977 | Buckner ................................. 128/75 |
| 4,583,533 | * | 4/1986 | Goodley et al. ....................... 128/75 |
| 4,881,528 | | 11/1989 | Scott . |
| 4,996,978 | * | 3/1991 | Gingras ................................. 128/78 |
| 5,224,924 | * | 7/1993 | Urso ...................................... 602/19 |
| 5,462,518 | * | 10/1995 | Hatley et al. ......................... 602/36 |
| 5,848,984 | * | 12/1998 | Bachar et al. ........................ 602/32 |
| 5,868,694 | * | 2/1999 | Marlow et al. ....................... 602/32 |

* cited by examiner

*Primary Examiner*—Denise Pothier
(74) *Attorney, Agent, or Firm*—Daniel C. McKown

(57) ABSTRACT

Rigid left and right side members extend vertically along the user's left and right sides. A girdle that encircles the user is suspended on adjustable straps from the upper ends of the rigid left and right side members. The adjustable straps on opposite sides of the girdle each have a first end permanently affixed to the inside surface of the girdle. The straps extend upward along the user's sides and pass through slots located near the tops of the rigid left and right side members. The straps then extend downwardly to second ends that are removably attached to the outside of the girdle at opposite sides by a hook-and loop fastener. In the front-to-rear direction, the rigid left and right side members coincide with the center of gravity of the lifted weight to avoid pitching moments. The straps by which the girdle is suspended are readily adjustable, thereby promoting the comfort of the user.

4 Claims, 2 Drawing Sheets

ORTHOPEDIC LUMBAR TRACTION SITTING DEVICE

REFERENCE TO RELATED APPLICATION

This application claims the benefit of U.S. Provisional Application No. 60/158,150, filed Oct. 8, 1999.

BACKGROUND OF THE INVENTION

1. Field of the Invention

The present invention is in the field of orthotics and specifically relates to an orthotic device that relieves some of the downward force on the user's lower spine when the user is seated.

2. The Prior Art

It has long been understood that most of the weight of the torso is transmitted to the pelvis through the spine, and that if this weight is reduced, for example by pulling upward on the torso, the pressure on the spinal dics and the nerves around them will be reduced, thereby reducing the pain that accompanies sitting.

An early approach to the problem was to provide a harness for suspending the torso from the back of a car seat. This was not satisfactory for users who needed to move from one location to another and from one seat to another.

A more recent approach is shown in U.S. Pat. No. 4,881,528 issued Nov. 21, 1989 to Scott. In Scott's device the seat is not part of the device, and this is certainly an improvement over earlier devices. Scott's device includes a rigid U-shaped frame the legs of which are about as far apart as the user's shoulder blades. This frame extends up along the user's back, and a girdle attached to the rigid frame pulls upwardly on the user's rib cage, thereby transferring some of the weight of the upper body to the rigid frame. The base of the frame rests on the seat.

This device is not entirely satisfactorily for the following reason. All parts of the user's body are located in front of the rigid frame, and therefore the center of gravity of any lifted weight must also lie in front of the rigid frame. To the extent that the device diverts some of the weight from the user's spine, to that extent a pitching moment is developed that tends to rotate the upper torso forward. The user must continually force his torso rearward if he wishes to sit up straight.

With this in mind, the present inventor set out to create a better device.

SUMMARY OF THE INVENTION

It occurred to the present inventor that to prevent the device from exerting an undesirable pitching moment on the user, it would be necessary to re-position the rigid load-supporting members forward to a location directly under the center of gravity of the relieved weight. Thus, in accordance with the present invention, the load bearing rigid portions of the device are located, not behind the back of the user, but instead along his left and right sides so that a downward projection of the center of gravity approximately falls on an imaginary line joining the lower ends of the load-bearing uprights.

The present inventor also was conscious of the fact that if the device were to be used for an extensive period of time, it must be comfortable. To remain comfortable, it is necessary occasionally to adjust the device in relation to the softness of various seats and in relation to the user's changing tolerance level. Accordingly, a preferred embodiment of the invention includes provision for adjusting the height of the girdle with respect to the rigid frame in a simple and convenient manner.

Thus, it is an objective of the present invention to provide a device having improved stability so that the user does not have to struggle to sit upright.

It is a further objective of the invention to provide a device that can readily be adjusted to accommodate seats of differing firmness.

In accordance with the present invention, these objectives are met by suspending a girdle by adjustable straps from the upper ends of load-bearing upright members, and by positioning the load-bearing upright members at the left and right sides of the user.

The novel features which are believed to be characteristic of the invention, both as to its structure and method of use, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
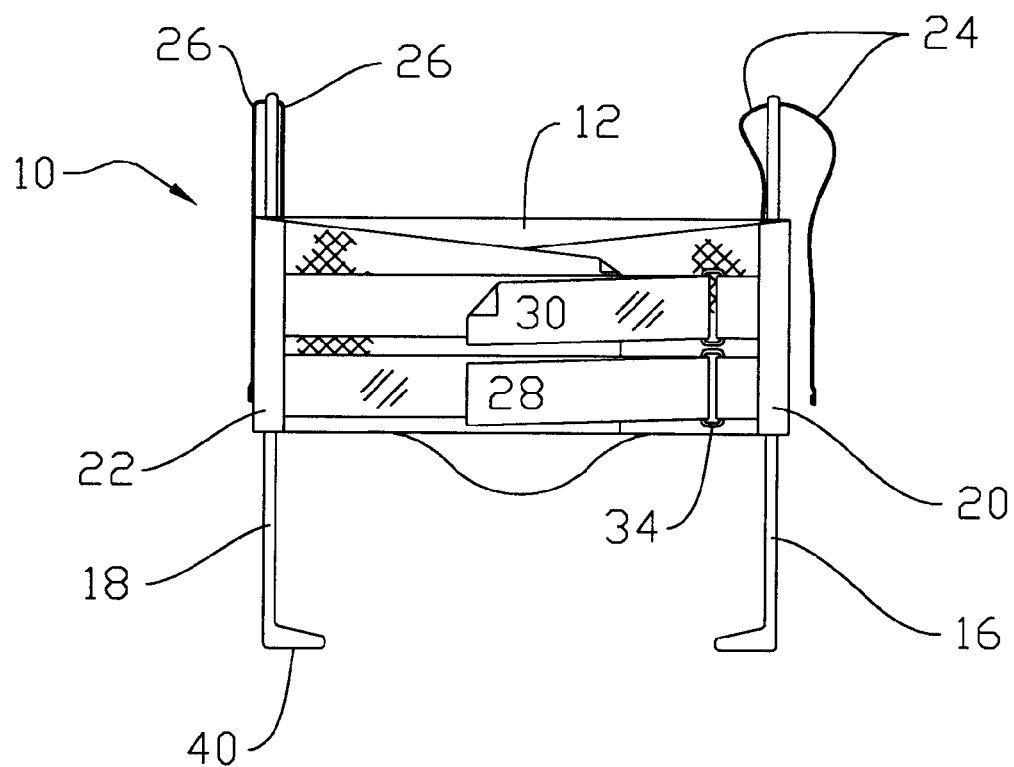
FIG. 1 is a front elevational view of a preferred embodiment of the device of the present invention; and, FIG. 2 is a side elevational view showing the embodiment of FIG. 1 in use.
Figure 2:
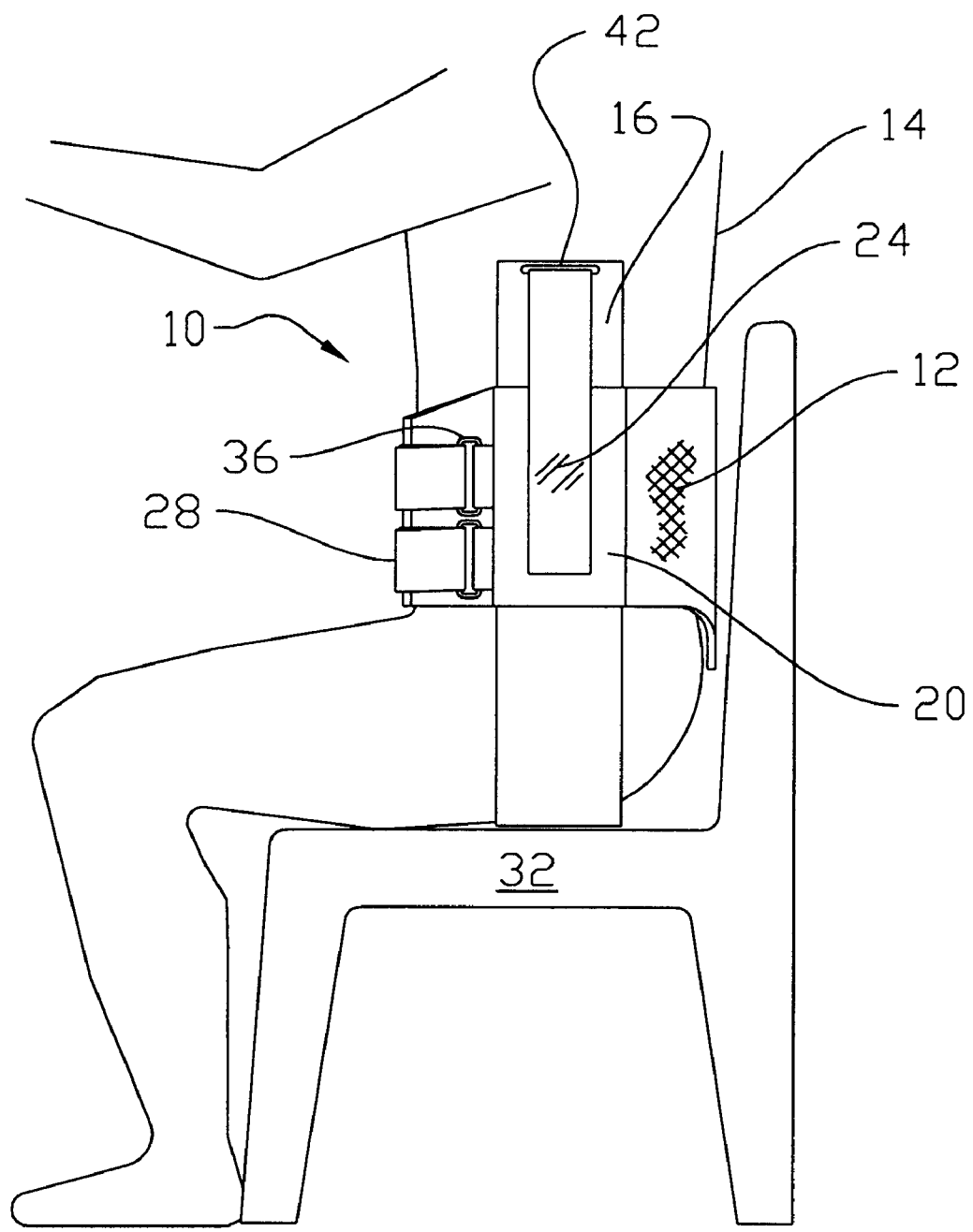

The orthopedic lumbar traction sitting device 10 can be best understood by a study of FIGS. 1 and 2 along with the following description. The lumbar traction sitting device 10 supports the upper body weight of a person 14 and translates it through the side members 16 and 18 into the chair 32 thus relieving spinal disc pressure, localized nerve pressure, and the pain associated with sitting. The rigid side members serve, in effect, as auxiliary spines, distributing some of the upper body weight to the seat.

The girdle 12 wraps around the torso of a person 14. The girdle 12 is secured to the torso of a person 14 by tightening straps 28 and 30. Tightening straps 28 and 30 slide through clips 34 and 36 thus creating a pulley like action and minimizing the pulling force necessary to obtain satisfactory tightness of the girdle 12. The straps 28 and 30 are fastened by hook and loop fastners or the like. The girdle 12 has attached tubular sleves or pockets 20 and 22 which allow the girdle to slide freely up and down on the side members. Load-bearing straps 24 and 26 are fixed on the inner circumference of the girdle 12, travel through an upper slot 42 on side members 16 and 18 and fasten to the attached pockets 20 and 22 on the outer circumference of girdle 12. Load-bearing straps 24 and 26 fasten to the outer circumference of girdle 12 by hook and loop fastners or the like. The side members 16 and 18 are positioned at the sides of a person 14 and offer stable support directly in line with the gravitational force of the upper body weight. Thus a substantial portion of the upper body weight of a person 14 is supported by a girdle 12, hangs on the load-bearing straps 24 and 26, and is transmitted down side members 16 and 18 into the chair 32.

The girdle 12 consists of several layers of cloth and padded material to give both stiffness and flexibility in supporting the upper body weight of a person 14. The girdle 12 is sewn together with nylon thread or the like. The side members 16 and 18 are rigid enough to support a substantial load and are preferably made out of plastic. The side members 16 and 18 have rounded edges and are contoured to the torso of a person 14. Each of the side members 16 and 18 has a foot 40 that spreads out the load to prevent damage to the chair 32. The tubular side pockets 20 and 22 are made out of a durable cloth and allow the side members 16 and 18 to pass through freely. The load-bearing straps 24 and 26 are preferably made of nylon webbing. The hook portion of the hook and loop is attached to the free end of the load bearing straps 24 and 26, and then attaches to the loop portion on the outer surface of the pockets 20 and 22 which are attached to the outer surface of the girdle 12. The tightening straps 28 and 30 are preferably made of nylon webbing and are secured by hook and loop or the like. The chair 32 can be any chair, seat, bench, automobile seat, truck seat, or airplane seat. The clips 34 and 36 are made out of plastic or metal and allow the tightening straps 28 and 30 to slide through freely.

To use the device, a person 14 wraps the girdle 12 around their torso while standing or sitting. The person then tightens the girdle using tightening straps 28 and 30. The person 14 then sits if not already doing so. To apply, or increase the amount of lumbar traction the user separates the hook and loop fastening of the load-bearing straps 24 and 26 and pulls down on the free end and then reattaches the hook to the loop to hold the new position. This action supports the upper body weight, relieves disc pressure, relieves localized pressure on the spinal nerves, and thus reduces the pain associated with sitting.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. An orthopedic lumbar traction sitting device worn by a user to reduce loading of the lumbar portion of the user's spine when the user is sitting on a seat, said device comprising:

left and right side members, substantially rigid, and extending vertically along the user's left and right sides respectively during use, each of said left and right side members having a lower end bearing down on the seat and having an upper end located at the level of the user's chest during use, and including a slot adjacent the upper end;

a girdle having an inside that faces the user when in use and having an outside that is exposed when in use, having an upper edge and a lower edge, and having left and right vertically-extending tubular side sleeves affixed to the outside of said girdle at the left and right sides of the user, when in use, each sleeve having an opening large enough to encircle said left and right side members so that said girdle is freely slidable up and down on said left and right side members;

left and right load-bearing straps each having a first end, the first ends permanently affixed to said girdle at the user's left and right sides respectively during use, said straps extending upward beyond the upper edge of said girdle, each of said load bearing straps passing through one of the slots adjacent the upper end of the respective left and right side members, and then extending downward to second ends that are removably attached to said girdle, so that the girdle may be raised with respect to said left and right side members by removably reattaching the second ends at a lower location on said girdle and so that the girdle may be lowered with respect to said left and right side members by removably reattaching the second ends at a higher location on said girdle, whereby said girdle is suspended by said left and right load-bearing straps, and whereby that portion of the user's weight that is supported by said girdle is removed from the lumbar portion of the user's spine and is transferred by said left and right load-bearing straps to said left and right side members.

2. The orthopedic lumbar traction sitting device of claim 1 wherein the first ends of said left and right load-bearing straps are permanently affixed to the inside of said girdle and wherein the second ends of said left and right load-bearing straps are removably affixed to one of said left and right vertically-extending tubular side sleeves of said girdle.

3. The orthopedic lumbar traction sitting device of claim 1 wherein said left and right side members each includes a foot at its lower end.

4. The orthopedic lumbar traction sitting device of claim 1 wherein said left and right side members are shaped to accommodate the user's sides and hips.

\* \* \* \* \*